(12) United States Patent
Frey et al.

(10) Patent No.: US 10,385,073 B2
(45) Date of Patent: *Aug. 20, 2019

(54) PROCESS FOR PREPARING ALKYL-INDIUM COMPOUNDS AND THE USE THEREOF

(71) Applicant: UMICORE AG & CO. KG, Hanau-Wolfgang (DE)

(72) Inventors: Annika Frey, Hanau (DE); Ralf Karch, Kleinostheim (DE); Andreas Rivas-Nass, Bensheim (DE); Eileen Woerner, Nidderau (DE); Angelino Doppiu, Seligenstadt (DE)

(73) Assignee: UMIICORE AG & CO. KG, Hanau-Wolfgang (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/550,136

(22) PCT Filed: Feb. 11, 2016

(86) PCT No.: PCT/EP2016/052882
§ 371 (c)(1),
(2) Date: Aug. 10, 2017

(87) PCT Pub. No.: WO2016/128498
PCT Pub. Date: Aug. 18, 2016

(65) Prior Publication Data
US 2017/0349610 A1 Dec. 7, 2017

(30) Foreign Application Priority Data
Feb. 13, 2015 (EP) .................................... 15155062

(51) Int. Cl.
*C07F 5/00* (2006.01)
(52) U.S. Cl.
CPC ...................................... *C07F 5/00* (2013.01)
(58) Field of Classification Search
None
See application file for complete search history.

(56) References Cited

U.S. PATENT DOCUMENTS

| 5,663,390 A | 9/1997 | Giolando |
| 2016/0207941 A1 | 7/2016 | Sundermeyer et al. |
| 2016/0207942 A1 | 7/2016 | Sundermeyer et al. |

FOREIGN PATENT DOCUMENTS

| DE | 3742525 A1 | 6/1989 |
| EP | 0372138 A1 | 6/1990 |
| WO | 2015024893 A1 | 2/2015 |
| WO | 2015024894 A1 | 2/2015 |

OTHER PUBLICATIONS

International Search Report for PCT/EP2016/052882, dated Apr. 25, 2016 in English Language.
Journal of Organometallic Chemistry, 40 (1972), p. C9-C10: The synthesis of lower alkylindium halides by the direct reaction between the metal and alkyl halides: Gynane, M. J. S., Waterworth, L. G. and Worrall, I. J.
Journal of Organometallic Chemistry, 43 (1972), p. 257-264: Oxidative addition reactions of group III metals in low oxidation states; Gynane, M. J. S., Waterworth, L. G. and Worrall, I. J.

*Primary Examiner* — Clinton A Brooks
(74) *Attorney, Agent, or Firm* — Smith, Gambrell & Russell, LLP

(57) ABSTRACT

The invention relates to a process for the cost-effective and environmentally responsible preparation of alkyl indium sesquichloride in high yield and with high selectivity and purity. The alkyl indium sesquichloride prepared in accordance with the invention is particularly suitable, also as a result of its high purity and yield, for preparation of indium-containing precursors in accordance with demand, in high yield and with high selectivity and purity. As a result of the high purity, the indium-containing precursors that are preparable are particularly suitable for metal-organic chemical vapor deposition (MOCVD) or metal-organic vapor phase epitaxy (MOVPE). The novel process according to the invention is characterized by the improved execution of the process, in particular by rapid process control. Owing to targeted and extensive use of raw materials that are inexpensive and have a low level of environmental pollution, the process is also suitable for use on an industrial scale.

29 Claims, No Drawings

PROCESS FOR PREPARING ALKYL-INDIUM COMPOUNDS AND THE USE THEREOF

The object of the invention is a process for preparing alkyl indium sesquichloride, characterized by the general formula R3In2Cl3 (hereafter also referred to as compound (A)) in high yield and with high selectivity and purity.

Likewise, as a result of such high purity and yield, the alkyl indium sesquichloride produced according to the invention is particularly suitable for preparation of indium-containing precursors in accordance with demand, preferably those having the general formula R3In (hereafter also referred to as compound (B)) or R2InR' (hereafter also referred to as compound (C)). The indium-containing precursors obtainable from compound (A) with high yield and in high purity are particularly suitable for organometallic chemical vapor deposition (MOCVD, also known as organometallic chemical vapor phase epitaxy, MOVPE).

To the extent the term "process" is used according to this invention, it always refers to the process for preparing compound (A) and the optional process for preparing indium-containing precursors based thereon, preferably compounds (B) or (C).

PRIOR ART

Various processes for preparing compounds are described in the prior art that are commonly used as organometallic precursors for MOCVD processes or their starting materials, respectively, referred to in the following simply as "starting material precursor,"

For purposes of this invention, "starting material precursors" are those which can be converted to the actual organometallic precursors through additional reaction steps (referred to briefly as "precursors" or "indium-containing precursors"), which can then be used directly in MOCVD processes. In doing so, it is advantageous to provide those starting material precursors, or to prepare precursors by means of such precursor starting materials which are themselves obtainable with high selectivity and yield. In addition, it can be very advantageous to provide precursor starting materials that can be prepared simply and with high purity and which, as the case may be, may be isolable and of sufficient storage stability to enable the adequate and fastest-possible preparation of high-purity precursors for MOCVD processes. MOCVD processes are used, in particular, to produce semiconductor layers for optoelectronic applications, such as solar cells or LEDs, but also to produce thin layers in other areas of application, which usually requires the highest possible purity of the respective precursor used, as well as the absence or the presence of only very small quantities of impurities, in particular those containing oxygen.

Thus, for example, various processes for preparing indium-containing, gallium-containing, or else aluminum-containing precursors or respective precursor starting materials are known. Nevertheless, the respective process conditions are not necessarily transferable, at least not without modification, between the elements. It must be noted that the elements aluminum, gallium and indium already exhibit different chemical behavior, regularly resulting in the need for an appropriately adjusted, particular tailored process regime in preparation of respective precursors.

Processes for preparing indium-containing precursors or precursor starting materials known in the prior art often encounter considerable difficulties when it comes to preparation in the purity and amounts necessary for customary uses, particularly with respect to reasonable costs as well. Thus, the electrical properties of semiconductor layers produced from indium-containing precursors using MOCVD can be significantly impaired by impurities in the precursors or precursor starting materials. Moreover, many preparation processes are very time-consuming. In addition, frequently only low yields are achieved, and the reaction steps are frequently characterized by reduced selectivity. In addition, based on the use of organic solvents in known preparation processes for preparing indium-containing precursors or precursor starting materials, the processes are generally cost-intensive, hardly environmentally friendly, and can be accompanied by organic solvent residues in the intermediate products and end products which, in turn, significantly restrict the use thereof or make costly and inconvenient purification necessary.

DE 37 42 525 A 1 relates to a process for preparing metal alkyls such as trimethyl indium, wherein preparation beginning with lithium tetramethylindate as precursor starting material by reaction with indium trichloride in an organic solvent is described. A mixture is obtained which comprises trimethyl indium which must subsequently still be isolated and purified. Even after purification, the reported yield is only 82% of the theoretical value. Preparation is also characterized by a relatively high process duration of more than 24 hours.

EP 0 372 138 A 1 describes a process for preparing organometallic compounds, according to which trialkylindium compounds are obtainable using a nonvolatile precursor starting material which can, for example, be lithiumtetramethylindate. The preparation of lithium tetramethylindate from indium trichloride takes place in diethyl ether with the addition of methyl lithium, which makes the entire process very costly overall. The lithium tetramethylindate is reacted with indium trichloride to give trimethyl indium, which must still be subsequently purified. No data are given for the actual yield. In addition, the described process is very costly due to numerous isolation and purification steps, among other things.

Gynane et al. describe the reaction of indium with alkyl bromides and alkyl iodides to give sesquihalides (Gynane, M. J. S, Waterworth, L. G. and Worrall, I. J., J. Organometal. Chem., 40, 1972). The reaction of indium monobromide or indium monoiodide with alkyl iodides or alkyl bromides to give alkyl indium dihalides is also described in an additional publication in which very long reaction times are necessary (Gynane, M J. S, Waterworth, L. G. and Worrall, I. J., J. Organometal. Chem., 43, 1972).

U.S. Pat. No. 5,663,390 relates to the preparation of alkyl metal chlorides by reaction of an alkyl chloride with elemental metal in the presence of H2 as a reaction accelerator. The latter is disadvantageous, however, particularly because the described process is very complex and the conversion is only incomplete. The reaction is overall very inconvenient and costly and is thus unsuitable on an industrial scale.

OBJECT

It is an object of the present invention to provide a process that enables inexpensive preparation, in accordance with demand, of suitable precursor starting materials for indium-containing precursors in a simple and rapid process. The said process must also enable preparation of such compounds with high yield and high purity. The precursor starting materials must furthermore be isolable in a simple manner and have sufficient storage stability.

In addition, the indium-containing precursors obtainable from the starting material must be as free as possible from oxygen impurities and obtainable in high yield and with high selectivity starting from the starting material. As a result, the indium-containing precursors so obtainable must be particularly suitable for MOCVD processes, which requires corresponding high-purity organoindium compounds for the production of semiconductor layers.

The process must also be performable with a low level of environmental pollution and with low resource intensity.

SOLUTION

The object of the present invention is solved by the subject-matter of the patent claims.

The object is solved in particular by a new process for preparing alkyl indium sesquichloride (compound (A)) having the general formula:

$$R_3In_2Cl_3,$$

where R is a lower alkyl radical, i.e. one having 1 to 4 carbon atoms. The alkyl radical can be branched or unbranched, preferably unbranched. Suitable alkyl radicals are thus isopropyl, cyclopropyl, isobutyl, sec-butyl, tert-butyl, but in particular propyl, n-butyl, as well as ethyl or methyl.

The structure of compound (A) has not yet been conclusively resolved and may also, instead of the formula given above, be interpreted as R3In2Cl3, as well as a mixture of R2InCl and RInCl$_2$. It is also possible that these compounds are in equilibrium with one another and/or with R3In2Cl3. The molar ratio of R2InCl and RInCl$_2$ to one another in compound (A) can be in the range of approximately 30:70 to 60:40, or from approximately 30:70 to 50:50, or from approximately 31:69 to approximately 45:55 or from approximately 32:68 to approximately 42:58. In the following, reference is also made to R3In2Cl3 or to alkyl indium sesquichloride, respectively, if the molar ratio of R2InCl and RInCl$_2$ in compound (A) produced deviates from the ideal ratio of 50:50.

Based on the starting substances used and further reagents used, the process is inexpensive and causes a low level of environmental pollution, and enables the preparation of R3In2Cl3 with rapid processing and high yield, as well as high purity. Organic solvents are not used.

It is additionally advantageous that compound (A) is isolable in a simple manner and has sufficient storage stability. On the other hand, compound (A) is also accessible to additional reaction steps without isolation, so that there is the possibility of the development of more cost-effective multi-step reactions without elaborate intermediate isolation (so-called one-pot reaction).

The process according to the invention is particularly suitable for the preparation of methyl indium sesquichloride Me3In2Cl3) and ethyl indium sesquichloride (Et3In2Cl3), or mixtures of Me2InCl/MeInCl2 and Et2InCl/EtInCl2 (sometimes also in non-stoichiometric ratios), most particularly for the preparation of Me3In2Cl3. R is thus preferably selected from ethyl and methyl; R is more preferably methyl. In the following, methyl and ethyl are abbreviated as Me for methyl and Et for ethyl.

According to the invention, therefore, a new process for the preparation of R3In2Cl3, i.e. compound (A), is first provided as a precursor starting material. Additional reaction steps may be joined to the process according to the invention, such that according to the invention indium-containing precursors for MOCVD processes are also obtainable more inexpensively and with a more rapid process regime, and in high yield and purity. The process according to the invention thus comprises the preparation of compound (A). In embodiments, the process according to the invention may be followed by the additional reaction steps for preparation of indium-containing precursors.

The indium-containing precursors are preferably selected from compounds having the general formula R3In (i.e. compound (B)) and R2InR' (i.e. compound (C)). As specified by the process according to the invention. R is the same in compounds (A), (B), and (C), while R' may deviate therefrom as further set forth below.

Thus, indium-containing precursors having the general formula:

$$R_3In,$$

are, according to the invention, those in which R is a lower alkyl radical having 1 to 4 carbon atoms. The alkyl radical can be branched or unbranched, preferably unbranched. R is, in particular, selected from ethyl and methyl; R is, in particular, methyl. For example, trimethyl indium or triethyl indium are highly useful as compounds having the formula RsIn.

Indium-containing precursors having the general formula:

$$R_2InR',$$

are, according to the invention, those in which R is a lower alkyl radical having 1 to 4 carbon atoms, which can be branched or unbranched, and wherein R' is a nucleophilic group that is different from R. R' is preferably selected from branched or unbranched and substituted or unsubstituted alkyl, branched or unbranched and substituted or unsubstituted aryl. R' can, in particular, be phenyl or alkyl substituted by branched or unbranched alkyl or alkoxy groups or amine radicals. Preferably, R' comprises alkyl or aryl groups having 1 to 6 carbon atoms which are substituted by branched or unbranched alkyl or alkoxy groups, such as methyl, ethyl, n-butyl, propyl, sec-butyl, tert-butyl, isobutyl, isopropyl, cyclopropyl, cyclobutyl, methoxy, ethoxy, n-butoxy, propoxy, sec-butoxy, tert-butoxy, isobutoxy, isopropoxy, cyclopropoxy, cyclobutoxy, or else alkyl or aryl groups having 1 to 6 carbon atoms, which are substituted (in particular monosubstituted or disubstituted) by amine radicals, which themselves are substituted by branched or unbranched alkyl groups, such as methyl, ethyl, n-butyl, propyl, sec-butyl, tert-butyl, isobutyl, isopropyl, cyclopropyl, and cyclobutyl.

For example, the nucleophilic group R' can be phenyl, toluyl, mesityl, dimethylamino, diethylamino, dibutylamino, diisopropylamino, Et2N—(CH2)3, Me$_2$N—(CH$_2$)3, Me$_2$N—(CH$_2$)2, Me$_2$N—CH$_2$, Et$_2$N—(CH$_2$)$_2$, Et$_2$N—CH$_2$, isopropyl, cyclopropyl, isobutyl, sec-butyl, tert-butyl, cyclopropyl, but in particular Me$_2$N—(CH$_2$)3-, propyl, n-butyl, as well as ethyl or methyl. If the definitions of R and R' encompass the same radicals, then in compound (C) R and R' must differ from each another. If, for example, R is methyl, then R' must be different from methyl.

In one embodiment of the invention, R is methyl and R' is a Me$_2$N—(CH$_2$)3 radical. In a further embodiment of the invention, R is methyl and R' is ethyl. In a further embodiment of the invention, R is ethyl and R' is methyl. Thus, the compounds Me$_2$InEt, Et$_2$InMe, as well as Me$_2$In—(CH$_2$)3-N-Me2 or (CH$_3$)2In—(CH$_2$)3-N—(CH$_3$)$_2$, are the result. In this embodiment, further reaction steps thus follow the process according to the invention, such that indium-containing precursors, preferably R$_3$In (i.e. compound (B)) or $R_2InR'$ (i.e. compound (C)), can also be obtained inexpensively and in accordance with demand, and with a rapid process regime.

The indium-containing precursors (B) and (C) obtainable with preference from compound (A) are, because of their particularly high purity, particularly useful for the production of indium-containing films, such as InP—, InAlP— or AlInGaP films, in the context of MOCVD processes and used in the semiconductor industry.

1. Process for the Preparation of Compound (A)

The process for preparing compound (A) having the general formula $R3In_2Cl3$ comprises the reaction steps of
- a1) reacting indium with an alkyl donor to form compound (A), wherein the alkyl donor is an alkyl chloride (RCl) and wherein R is a branched or unbranched alkyl group having 1 to 4 carbon atoms;
- a2) optional isolating compound (A) from the reaction mixture;

wherein in reaction step a1) a compound having the formula R3In2Cl3 is used as the reaction medium and the ratio of indium to the reaction medium is 0.5:10 to 1.4:0.5 or 0.5:3 to 1.4:0.5, in particular 1:2 to 2:1 or 1:1.5 to 1.5:1 (relative to weight). No separate activator or organic solvent is used.

Reaction Step a1):

The indium can be used at a purity of preferably at least 5N or higher (corresponding to >99.999% metallic purity relative to the indium), although 4N (=99.99% metallic purity) indium can also be used. In principle, however, the use of lower purity indium is also possible. The particle size can be varied within broad limits since the indium is present in molten form at the reaction temperature (the melting point of indium being approximately 156° C.). For example, to make dimensioning of the necessary amounts and filling the reactor easier, granules having a particle size of 1 mm to 10 mm, in particular 4 mm to 6 mm, can be used (e.g. so-called indium shots approximately 0.5 cm in size), but powder or even ingots can also be used.

The alkyl donor is a compound that comprises an alkyl radical, wherein the alkyl donor is an alkyl halide, wherein alkyl is defined as above and chlorine, bromine, or iodine can be used as the halide, in particular chlorine. Thus, the alkyl donor can in particular be an alkyl chloride, thus also comprising at least one chlorine atom in addition to the alkyl group. The alkyl donor is in particular an alkyl halide (in particular an alkyl chloride), wherein alkyl is defined as above (see the definition of R); alkyl methyl or ethyl is particularly preferred, in particular methyl. In preferred embodiments the alkyl donor is thus methyl chloride (chloromethane) or ethyl chloride (chloroethane); methyl chloride is particularly preferred.

Preferably, 1.5 to 5 equivalents of alkyl donor per equivalent of indium are used for this reaction, or 1.65 to 4.5 equivalents or 1.65 to 3 or 1.65 to 2.9 equivalents of alkyl donor per equivalent of indium are used. If the proportion of alkyl donor used is too small relative to the indium, there is the danger of an incomplete reaction and a reduced yield of compound (A). If the proportion of alkyl donor used is too large relative to the indium, then the process is too expensive and uneconomical overall and it can no longer be carried out economically on an industrial scale, which is undesirable.

Preferably, the indium and the alkyl donor are added to the reaction vessel consecutively. It is particularly preferred that indium and the reaction medium are provided in the reaction vessel first, and the alkyl donor is added thereafter. Surprisingly, this led to high yields and also simplifies the apparatus required. Thus, indium and the reaction medium, compound (A), can simply be weighed into the reactor.

Thereafter, a controlled addition of the alkyl donor can take place. The reaction medium melts upon warming up to the reaction temperature and forms a transparent melt in which the likewise liquid indium can be present as an emulsion or as a second liquid phase.

The addition of the alkyl donor to the indium is preferably carried out in such a way that the alkyl donor, which is preferably present in gaseous form at standard conditions (boiling point of MeCl is −24° C., that of EtCl is 12° C.), by the controlled, constant introduction into the reaction in liquid or gaseous state. In the reactor, respectively under reaction conditions, the alkyl donor is present in gaseous form.

Upon introduction, as much alkyl donor is preferably constantly supplied as is required so that the reaction (over) pressure is kept constant throughout the course of the reaction. Control is provided, for example, automatically by means of a pressure sensor coupled to a metering valve.

Optionally, the alkyl donor can be added by means of condensation.

The alkyl donor is preferably added to the reactor in liquid form. As a rule, the total amount of alkyl donor required is not added from the outset, as is the case with condensation, but instead alkyl donor is continuously metered into the mixture of indium and reaction medium, compound (A), until the reaction is complete.

Metering of the liquid alkyl donor can then take place under pressure directly from the liquid gas tank. The alkyl donor immediately vaporizes in the reactor owing to the prevailing reaction conditions, so that the reaction with the gaseous alkyl donor takes place in the reactor.

The addition of the alkyl donor by means of introduction or pressure is generally initiated at temperatures exceeding 20° C. In one embodiment, the indium or the mixture of indium and the reaction medium, compound (A), is present in the reactor in liquid form when addition of the alkyl donor is commenced. Since pure indium has a melting point of 156.6° C., addition takes place at a temperature of 156° C. or higher. This means that, in this embodiment, indium and the reaction medium are provided in the reactor and are heated until the mixture is liquid, whereupon addition of the alkyl donor is commenced.

In a further embodiment the alkyl donor, for example methyl chloride, is passed into the reactor at room temperature with the provided indium reaction-medium mixture, and then heated to the desired reaction temperature, during which time introduction of the alkyl donor continues.

After initiation of the addition of the alkyl donor, the reaction mixture is heated. A temperature of 250° C., preferably 235° C. is thus preferably not exceeded in order to avoid side reactions, as well as for economic considerations. At reaction temperatures greater than 235° C. a slow thermal decomposition can be observed in which indium, presumably, emerges as a decomposition product. Heating to temperatures of at least 156° C. is preferred, more preferably to at least 170° C. and most preferably to at least 180° C., in order to enable a particularly complete reaction to compound (A). Thus, the reaction temperatures are in the range from approximately 156° C. to approximately 250° C., or from 180° C. to 200° C., notwithstanding the manner in which the addition of the alkyl donor takes place.

Reaction step a1) can be conducted under an inert gas, such as argon or nitrogen. However, it is possible to conduct the reaction without additional inert gas in a pure atmosphere of alkyl donor, such as for example methyl chloride or ethyl chloride, which has advantages.

In general, the addition of the alkyl donor takes place at a given constant pressure, for example at an absolute pressure of 1 bar to 7 bar, or 2 bar to 5.5 bar, or 2.5 bar to 5 bar (overpressure of 0.1 bar to 6 bar, or 1 bar to 4.5 bar, or at 1.5 bar to 4 bar). In doing so it is possible to proceed such that a desired overpressure of alkyl donor (e.g. ethyl chloride or methyl chloride), for example 3.5 bar, is set. As much alkyl donor (e.g. ethyl chloride or methyl chloride) as is consumed is constantly supplied to the reactor by means of a flow regulator, so that the pressure in the reactor remains somewhat constant at, for example, 4.5 bar (or the overpressure at 3.5 bar, respectively). When no more alkyl donor (e.g. ethyl chloride or methyl chloride) is consumed, then the reaction is finished.

Since gaseous secondary products, such as ethane or methane, can emerge during the reaction, it has proved worthwhile to occasionally release the overpressure in the reactor and to resupply it with alkyl donor. This can be of particular advantage if the presence of indium can indeed be observed, but no consumption of alkyl donor, which is inevitably the case if a reaction of indium with the alkyl donor is taking place.

A particular advantage in the use of the product alkyl indium sesquichloride or the mixture of Me2InCl/MeInCl2 itself as reaction medium lies in the fact that, in a simple reaction, a part of the reaction product is left behind in the reactor to be used in the next batch and, besides indium and the alkyl donor, no additional chemicals are required, such that preparation of compound (A) can be driven semi-continuously.

The reaction medium is preferably used in such an amount that the molar ratio of indium to reaction medium is at least 1:1. Molar ratios of indium to reaction medium, compound (A), of up to 8:1, in particular <4:1, for example 3.8:1 or 3.5:1, have proven valuable, such that the molar ratios of indium to reaction medium are in the range from 1 to 8:1, in particular 1:1 to <4:1, or 1:1 to 3.8:1, or 1:1 to 3.5:1.

Particularly in the presence of non-stoichiometric mixture ratios of R2InCl and RInCl$_2$ in compound (A) it is simpler to state the ratio of indium to reaction medium used not as a molar ratio, but rather as proportions. The proportions of indium to reaction medium, compound (A) having the formula R3In2Cl3, are within the range of approximately 0.5:10 to 1.4:0.5 or from approximately 0.5:3 to approximately 1.4:0.5, in particular 1:2 to 2:1 or 1.1.5 to 1.5:1.

The reaction time of step a 1) is preferably between 10 min and 30 hours. A reaction time of at least 15 min, more preferably of at least 30 min, and even more preferably of at least 40 min has proven itself to be particularly advantageous with respect to the yield of compound (A). The reaction time is more preferably at most 28 hours, most preferably at most 12 hours. Too-long reaction times lead to a very cost-intensive and uneconomical process.

In all embodiments of the process according to the invention the following reaction, in schematic form, proceeds in reaction step a 1):

2In +3RCl ⟶ R$_3$In$_2$Cl$_3$

or 2In +3RCl ⟶ R$_2$InCl+RInCl$_2$,

If R3In2Cl3 is interpreted as mixtures of R2InCl and RInCl$_2$.

Reaction Step a2):

The isolation of compound (A), which is optional in accordance with the invention, preferably comprises the separation of volatile constituents from the reaction mixture present in the reaction vessel and/or process steps selected from the sublimation of compound (A) from the reaction mixture and the mechanical removal of compound (A) from the reaction vessel. The release of the product in liquid state can be regarded as a simple variation of mechanical removal.

The term "isolation" or respectively "to isolate" thus encompasses the separation of the particular desired reaction product from the reaction mixture present in the reaction vessel by removing the reaction product from the reaction vessel, or removing other compounds besides the reaction product from the reaction mixture in such a way that only the reaction product remains in the reaction vessel.

In one embodiment, compound (A) is isolated by means of removal from the reaction vessel, which can be accomplished using spoons, spatulas, scrapers, etc. Release in the liquid state is a very simple possibility, which can be accomplished by means of draining through an appropriate valve or by means of forcing the liquid into a container by pressure. It has been found to be particularly advantageous for the purity of compound (A) to first separate volatile secondary components from the mixture found in the reaction vessel, in particular alkyl donor still present, for example methyl chloride or ethyl chloride, and only thereafter to remove compound (A) from the reaction vessel. The removal of secondary components, in particular any alkyl donor RCl still present, is preferably done by applying a vacuum. In doing so a vacuum having a residual gas pressure below 1 hPa, more preferably below 0.1 hPa, has proven useful.

Optionally, additional steps for the purification of compound (A) can be joined to the isolation of compound (A), wherein suitable processes for purifying chemical substances are known to the person skilled in the art. According to the invention, a sufficiently high purity of compound (A) is preferably already achieved through the particular process and reactants according to the invention, even without additional purification steps. Preferably in accordance with the invention, therefore, aside from the preferred isolation of compound (A), no further purification steps of compound (A) are required, i.e. the separation of volatile secondary components and the removal of compound (A) from the reaction vessel.

Only an incomplete removal of the reaction product from the reaction vessel takes place during the isolation of compound (A). The amount of compound (A) remaining in the reaction vessel will be used in the next batch after the addition of further indium and re-addition of alkyl donor as reaction medium for the further preparation of compound (A). In doing so, the amount of reaction product, compound (A), calculated on the basis of the amount of indium used, is generally removed.

In alternative embodiments, no isolation of compound (A) from the reaction mixture takes place. In such embodiments the reaction mixture comprising compound (A) is used directly for preparing indium-containing precursors, in particular compound (B) or (C). In these embodiments additional reaction steps for preferably preparing compound (B) or (C) follow directly on from reaction step a 1), without an isolation of compound (A) from the reaction mixture, i.e. without reaction step a2). This enables an even more rapid process regime in preparing indium-containing precursors.

The process according to the invention enables preparation of compound (A) with a yield preferably of at least 70%, more preferably at least 75%, even more preferably at least 79% and most particularly preferably at least 85%, and even more preferably above 90% and even more preferably above 95%. Yield data given for the invention are always based on the theoretical yield.

The purity of compound (A) prepared in accordance with the invention is preferably at least 95%, preferably at least 98% and particularly preferably more than 99%. Thus, preferably not more that 5%, preferably not more than 2% and more preferably less than 1% impurities, i.e. unwanted substances, are present in the compound (A) prepared.

One preferred compound (A), which is obtainable according to the inventive process, is selected from methyl indium sesquichloride (Me3In2Cl3) which, as described above, can also be interpreted as a mixture of Me2InCl and MeInCb, and ethyl indium sesquichloride (Et3In2Cl3) which, as described above, can also be interpreted as a mixture of Et2InCl and EtInCb. The process according to the invention is most particularly suited to preparing Me3In2Cl3.

2. Further Processing of Compound (A) to give Indium-Containing Precursors

The compound (A) obtained according to the above-described process can optionally be processed further to give indium-containing precursors, preferably selected in accordance with the invention from compounds (B) and (C). The invention, therefore, also includes the use of compound (A) obtained according to the invention for preparation of indium-containing precursors, preferably selected from compounds (B) and (C), for MOCVD or MOVPE processes.

The compound (A) prepared in accordance with the invention is particularly suitable for preparing indium-containing precursors having the general formula:

$R_3In$, i.e., compound (B) wherein R is a lower alkyl radical having 1 to 4 carbon atoms. The alkyl radical can be branched or unbranched, preferably unbranched, R is preferably selected from ethyl and methyl, where R is in particular methyl. Due to the nature of the process, R is determined by the R group in compound (A), so that R in compound (A) corresponds to the R group in compound (B).

One embodiment thus relates to a process for preparing a compound (B) of the general formula RsIn comprising the reaction steps of
    providing compound (A) as described above, or according to one of claims 1 through 12;
    reacting compound (A) with an alkylating agent. The alkylating agent can be selected from R—MgX, R—Li and R3Al, where R is defined as above.

This reaction can be conducted in the presence of organic solvents, such as ethers, aliphatic or aromatic hydrocarbons, as well as their combinations. Dialkyl ethers are particularly suitable. Most particularly preferably, a solvent selected from diethyl ether, methyltetrahydrofuran, longer-chain ethers and mixtures thereof are used in the reaction step, wherein longer-chain ethers are those having alkyl radicals comprising more than 2 C atoms, in particular diethyl ether or di-n-butyl ether, more preferably diethyl ether. Alkanes, including cycloalkanes and aromatics can be used as aliphatic or aromatic hydrocarbons, such as n-pentane, n-heptane, n-hexane or benzene. In particular, alkanes and aromatics having high boiling points, for example n-decane, n-nonadecane, squalene and naphthalene, have proven to be particularly suitable as organic solvents for this step. Thereafter, optional additional purification steps for preparing high-purity compound (B) can be conducted.

Alternatively, the compound (A) produced according to the invention can be used to produce indium-containing precursors having the general formula:

$R_2InR'$ i.e. compound (C), wherein R is a lower alkyl radical having 1 to 4 carbon atoms, which can be branched or unbranched, and wherein R' is a nudeophilic radical different from R. R' is preferably selected from branched or unbranched and substituted or unsubstituted alkyl, branched or unbranched and substituted or unsubstituted aryl.

R' can, in particular, be phenyl or alkyl substituted by branched or unbranched alkyl or alkoxy groups, or by amine radicals. In particular, R' comprises alkyl or aryl radicals having 1 to 6 carbon atoms which are substituted by branched or unbranched alkyl or alkoxy groups, such as methyl, ethyl, n-butyl, propyl, sec-butyl, tert-butyl, isobutyl, isopropyl, cyclopropyl, cyclobutyl, methoxy, ethoxy, n-butoxy, propoxy, sec-butoxy, tert-butoxy, isobutoxy, isopropoxy, cyclopropoxy, cyclobutoxy, or else alkyl or aryl radicals having 1 to 6 carbon atoms, which are themselves substituted (especially monosubstituted or disubstituted) by amine radicals, which themselves are substituted by branched or unbranched alkyl groups, such as methyl, ethyl, n-butyl, propyl, sec-butyl, tert-butyl, isobutyl, isopropyl, cyclopropyl, and cyclobutyl.

The nudeophilic group R' can, for example, comprise phenyl, toluyl, mesityl, dimethyl amino, diethyl amino, dibutylamino, diisopropylamino, Et2N—(CH2)3, Me2N—(CH$_2$)3, Me$_2$N—(CH$_2$)2, Me$_2$N—CH$_2$, Et$_2$N—(CH$_2$)$_2$, Et$_2$N—CH$_2$, isopropyl, cyclopropyl, isobutyl, sec-butyl, tert-butyl, cyclopropyl, but in particular Me$_2$N—(CH$_2$)3, propyl, and n-butyl, as well as ethyl or methyl. If the definitions of R and R' encompass the same radicals, then in compound (C) R and R' must differ from each another. If, for example, R is methyl, then R' must be different from methyl.

In one embodiment of the invention, R is methyl and R' is a Me$_2$N—(CH$_2$)3 radical. In a further embodiment of the invention, R is methyl and R' is ethyl. In a further embodiment of the invention, R is ethyl and R' is methyl. Thus, the compounds Me$_2$InEt, Et$_2$InMe, as well as Me$_2$In—(CH$_2$)$_3$—N-Me$_2$ or (CH$_3$)$_2$In—(CH$_2$)$_3$—N—(CH$_3$)$_2$ are the result.

Due to the nature of the process, R is determined by the R group in compound (A), so that R in compound (A) corresponds to the R group in compound (C).

2.1. Further Processing of Compound (A) to give Compound (B)

In preferred embodiments, the preparation of compound (A) is additionally followed by the following further reactions steps, wherein compound (B) is obtainable:
    b1) reacting compound (A) with an alkyllithium to form lithium tetraalkylindate (LiInR$_4$), and isolating LiInR$_4$ from the reaction mixture, and
    b2) reacting the LiInR* with an indium chloride component, wherein compound (B) is obtained.

Reaction step b2) may directly follow on from reaction step b1). Alternatively, reaction step b2) can also be effected with a time offset from reaction step b1).

Reaction Step b1)

Reaction step b1) comprises the reaction compound (A) with an alkyl lithium to form lithium tetraalkylindate, wherein the lithium tetraalkylindate satisfies the following general formula:

$LiInR_4$ wherein R is defined as above. R is advantageously methyl or ethyl, in particular methyl. Due to the nature of the process, R is determined by the R group in compound (A).

The term "alkyllithium" encompasses those compounds which comprise at least one alkyl group and lithium. According to the invention, alkyllithium has the following general formula:

RLi wherein R is defined as above. The alkyl lithium is most particularly preferably selected from ethyl lithium (EtLi) and methyl lithium (MeLi), the alkyl lithium being in particular methyl lithium.

The alkyl lithium is used in reaction step b1) as an alkylating agent, but not as a reducing agent.

Reaction step b1) preferably takes place in an organic solvent. Dialkyl ethers are particularly suitable as organic solvents for step b1). A solvent selected from diethyl ether, diethoxymethane, methyltetrahydrofuran, longer-chain ethers and mixtures thereof are most particularly preferably used in reaction step b1), wherein longer-chain ethers are those having alkyl groups comprising more than 2 C atoms. Even more preferably, the solvent is diethyl ether or di-n-butyl ether, diethyl ether being more preferred.

It has proven to be particularly advantageous to use between 4 and 5.3 equivalents of alkyl lithium per equivalent of compound (A), particularly preferably between 4.8 and 5.3 equivalents, and even more preferably between 4.8 and 5.2 equivalents, and most particularly preferably approximately 5 equivalents.

In preferred embodiments the alkyl lithium is charged in the organic solvent first and compound (A) is added subsequently, preferably at temperatures between −10 and 10° C., more preferably at temperatures between −5 and 5° C., more preferably at −2 to 2° C. and even more preferably at 0+/−1° C. The reaction preferably takes place at temperatures between −30° C. and the boiling point of the organic solvent, more preferably at −5° C. to 35° C.

In alternative embodiments compound (A) is charged in the organic solvent first and the alkyllithium is added thereafter. In doing this the alkyllithium is preferably added dropwise as a mixture with the organic solvent, particularly preferably at temperatures between −10 and 10° C., more preferably between −5 and 5° C. and even more preferably at −2 to 2° C.

Subsequent to the addition of all reagents preference is given to stirring for preferably at least 10 min, more preferably at least 15 min. The reaction time is generally not more than 48 hours, preferably not more than 24 hours.

LiInR$_4$ is isolated from the reaction mixture. This occurs preferably by removal of the solvent and any by-products, in particular LiCl, or residues of the reagents, preferably by distilling off volatile constituents and/or filtering the reaction mixture. Isolation of the LiInR$_4$ by filtration to remove LiCl and subsequent removal of the solvent by distillation has been found to be particularly advantageous.

In a preferred embodiment the following reaction, in schematic form, proceeds in reaction step b1):

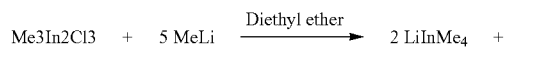

Me3In2Cl3 + 5 MeLi $\xrightarrow{\text{Diethyl ether}}$ 2 LiInMe$_4$ + 3 LiCl

Reaction Step b2):

Compound (B) is preparable from LiInR* by reaction of LiInR* with an indium chloride component.

The "indium chloride component" is, according to the invention, a compound that comprises indium and chloride.

The term "indium chloride component" also includes, in particular, compounds also having at least one alkyl radical in addition to indium and chloride. The indium chloride component preferably has the following general formula:

RaIribClc, where a is a number selected from 0, 1, 2, and 3 and b is a number selected from 1 and 2 and c is a number selected from 1, 2, and 3, and where a+b+c=4 or a multiple of 4, particularly preferably the sum of a, b and c=4 or 8. R is a lower alkyl radical having 1 to 4 carbon atoms. The alkyl radical can be branched or unbranched, preferably unbranched. R is preferably selected from ethyl and methyl, where R is, in particular, methyl.

The indium chloride component selected from InCb, R2InCl, R3In2Cl3, RInCl$_2$ and mixtures thereof is most particularly preferred. Most particularly preferred indium chloride components are R2InCl or R3In2Cl3, in particular Me2InCl, Et2InCl, Me3In2Cl3 or Et3In2Cl3, more preferably Me2InCl or Me3In2Cl3. Compound (A) is preferably used, which makes the process according to the invention even more economical. In particularly preferred embodiments the indium chloride component is thus R3In2Cl3, i.e., compound (A). The indium chloride component is advantageously obtained with the reaction steps a1) and a2) described above.

The molar ratio of lithium tetraalkylindate to the indium chloride component can be between 1:1 to 3:1, preferably approximately 1:1, 2:1 or 3:1. In embodiments in which the indium chloride is R2InCl, a molar ratio of lithium tetraalkylindate to the indium chloride component of approximately 1:1 has been found to be particularly advantageous. In embodiments in which the indium chloride component is R$_3$In$_2$Cl$_3$, a molar ratio of lithium tetraalkylindate to the indium chloride component of approximately 3:1 has been found to be particularly advantageous. In embodiments in which the indium chloride component is RInCl$_2$, a molar ratio of lithium tetraalkylindate to the indium chloride component of approximately 2:1 has been found to be particularly advantageous.

The reaction of lithium tetraalkylindate with the lithium chloride component can take place in an organic solvent. Suitable organic solvents for step b2) are selected from alkanes, including cyclic saturated hydrocarbons, aromatics, alcohols, ethers, and cyclic ethers. Alkanes and aromatics have proven to be particularly suitable as solvents for step b2), preferably selected from n-pentane, cyclohexane, n-decane, n-heptane, n-hexane, methylcyclohexane, n-nonane, n-octane and benzene, with n-pentane being most particularly preferred.

In alternative embodiments no organic solvent is used in reaction step b2), i.e. no organic solvent is used additionally as reaction medium. This has the advantage that any possible organic contaminations which restrict usability in compound (B) that result from partial breakdown of the solvent are avoided. In addition, the process can thus be carried out in a more environmentally responsible manner. Thus, in one embodiment step b2) is performed in the absence of organic solvents.

The LiInR$_4$ is preferably provided in the reactor with the indium chloride component. Thereafter, the organic solvent can be added. It is then preferably heated, preferably to temperatures between 30° C. and 120° C., more preferably to temperatures between 40° C. and 100° C. and even more preferably to temperatures between 50° C. and 90° C. Such a temperature is preferably maintained for at least 10 min and at most 24 hours, preferably for at least 30 min and at most 20 hours, more preferably at least 40 min and at most 12 hours, and even more preferably for at least 90 min and at most 3 hours.

It is next preferably cooled, preferably to a temperature of 25+/−5° C.

Compound (B) is then preferably isolated from the mixture. The isolating of compound (B) preferably comprises the removal of the organic solvent and compound (B) from the reaction mixture, which may contain salts, such as lithium chloride LiCl, for example. This occurs in particular through there condensation of organic solvents and compound (B) into a new vessel. For this purpose, all volatile components such as compound (B) (e.g. trimethyl indium) are, together with the solvent, distilled from the residue under vacuum (e.g. salts, such as LiCl). Thereafter, the solvent is separated from compound (B), preferably by distillation in a vacuum, preferably with a residual gas pressure of less than 0.1 hPa, more preferably a maximum of 0.01 hPa, preferably into a cold trap at preferably −10°+1-5° C. Compound (B), for example trimethyl indium or triethyl indium, then remains in the vessel. Optionally, further purifying steps may follow according, by purifying processes known to those skilled in the art. Such further purification steps can include distillation, sublimation, or recrystallization of compound (B).

In a preferred embodiment the following reaction, in schematic form, takes place in reaction step b2):

LiInMe$_4$+Me$_2$InCl ⟶ 2Me$_3$In+LiCl

In an alternative embodiment in which the indium chloride component is compound (A), the following reaction, in schematic form, takes place in reaction step b2):

3LiInMe$_4$+Me$_3$In$_2$Cl$_3$ ⟶ 5Me$_3$In+3LiCl

The additional reaction steps including b1) and b2) enable the preparation of compound (B) from compound (A) with a yield of preferably at least 60%, more preferably at least 70%, even more preferably at least 75% and most preferably 85% and even more preferably above 90%. The purity of compound (B) prepared in accordance with the invention is preferably at least 99%, preferably at least 99.5% and more preferably greater than 99.8% and even more preferably greater than 99.999% In particular, in performing a further step for purifying the compound (B) prepared, preferably by sublimation of compound (B), a purity of >99.999% can be achieved.

2.2. Further Processing of Compound (A) to give Compound (C)

In alternative embodiments compound (A) is further processed to give compound (C), wherein further reaction steps are added onto the process according to the invention, comprising:

c1) separating dialkyl indium chloride (R2InCl) from compound (A), and
c2) reacting R2InCl with an alkylating agent to form compound (C).

Dimethylaminopropyl dimethyl indium (DADI) or ethyl dimethyl indium (Me2InEt) are particularly preferred as compound (C).

In process step c1) there Is separation of dialkyl indium chloride from R$_3$In$_2$Cl$_3$ which, as described above, can also be considered as a mixture of R2InCl and RInCl$_2$, wherein the dialkyl indium chloride is characterized by the general formula R2InCl, wherein R is as defined above and can advantageously be methyl or ethyl, in particular methyl, wherein R is determined by the "R" group in compound (A). The separation of R2InCl from compound (A) can be accomplished by sublimation. To do so, compound (A) is preferably heated to temperatures between 150° C. and 200° C., more preferably between 155° C. and 195° C., and in particular between 160° C. and 190° C. The sublimation can optionally be carried out in a vacuum. In doing so, a vacuum preferably having a residual gas pressure below 1 hPa, more preferably below 0.1 hPa, has been found to be valuable. It is known to those skilled in the art that, when conducting process step c) in a vacuum, the separation of R2InCl can also be carried out at correspondingly lower temperatures. Separation into a sediment and a sublimate is preferably carried out, wherein the sublimate is preferably R2InCl.

Through the addition of one or more alkali halides, such as KCl, but also KF or other MX, where M=Na, K, or Cs and X=F, Cl, Br, or I) or a mixture of NaCl and KCl, the yield during the sublimation can be increased significantly and R2InCl can be completely separated.

In a preferred embodiment the following schematic reaction takes place in reaction step c1):

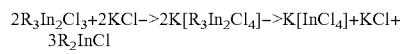
2R$_3$In$_2$Cl$_3$+2KCl−>2K[R$_3$In$_2$Cl$_4$]−>K[InCl$_4$]+KCl+3R$_2$InCl Reaction step c1) commonly occurs under a protective gas, for example argon or nitrogen. Alternatively, dialkyl indium chloride R$_2$InCl can also be produced in situ from R3In$_2$Cl3 (compound (A)) and further converted directly to compound (C) using alkylating agents.

The alkylating agent in step c2) is, in particular, selected from R'MgX, R'Li and R'3Al, wherein R' is defined as above. The alkylating agent Me$_2$N—(CH$_2$)3-M is particularly preferred, where M is, in particular, MgCl or Li, or even ethyl lithium (EtLi).

The conversion of R$_2$InCl to R$_2$InR', for example DADI, can take place in an organic solvent by reaction with the alkylating agent, for example Me$_2$N—(CH$_2$)3-M in the case of DADI. The organic solvent can be a dialkyl ether or a cyclic ether or mixtures thereof, in particular diethyl ether or THF, more preferably THF.

Reaction step c2) commonly takes place under protective gas.

Preferably, the alkylating agent is preferably provided in the organic solvent, in particular THF, and R$_2$InCl is subsequently added. In so doing, R$_2$InCl is particularly preferably added dropwise as a mixture with the organic solvent, in particular THF. The dropwise addition of R$_2$InCl preferably takes place slowly, preferably over at least 10 min, more preferably over at least 20 min. The addition of R$_2$InCl preferably takes place at a temperature below 50° C., more preferably below 40° C., and particularly preferably at room temperature, i.e. 25° C.+/−5° C.

After addition of all reagents, in particular alkylating agent and R$_2$InCl, stirring preferably takes place. The temperature during stirring is preferably below 50° C., more preferably below 40° C., and particularly preferably at room temperature, i.e. 25° C.+/−5° C. It is preferably stirred for at least 5 hours, more preferably for at least 10 hours. For reasons of cost, reaction times of 80 hours, more preferably 50 hours, are preferably not exceeded.

Thereafter, compound (C) is preferably isolated from the reaction mixture. The isolation of compound (C) can include the removal of the organic solvent, preferably in a vacuum, and the separation of compound (B) from the reaction mixture through filtration and/or distillation.

The alkylating agents can be produced using known processes, for example Me2N—(CH2)3-M from 3-chloro-1-(dimethylamino)propane by reaction with magnesium shavings or lithium shavings. The preparation of Me2N—

(CH2)3-M usually occurs in an organic solvent, in particular THF, under heating. In doing so, iodine can possibly be used for activation. Other known alkylating agents are commercially obtainable. By observing the requirements of the preparation process presented above for preparing compound (A), and optionally the further processing to indium-containing precursors, preferably selected from compound (B) and (C), these compounds can be produced in high yield and with high purity. In accordance with the invention, moreover, the compound (A) prepared according to the process, in particular Me3In2Cl3, and the indium-containing precursors obtainable therefrom, in particular trimethyl indium and dimethylaminopropyl dimethyl indium, as well as R2InCl. Therefore, the present patent application relates as well to the use of compound (A) according to the present patent application for the preparation of compound (B) according to claim, and the use of compound (A) according to the present patent application for the preparation of compound (C).

The present patent application further relates to a process for preparing an indium chloride component of the general formula:

$$R_aIn_bCl_c,$$

where a is a number selected from 0, 1, 2, and 3, and b is a number selected from 1 and 2, and c is a number selected from 1, 2, and 3, and where a+b+c=4 or a multiple of 4, particularly preferably the sum of a, b and c=4 or 8, where R is an alkyl radical having 1 to 4 carbon atoms, the alkyl radical can be branched or unbranched and can in particular be ethyl or methyl, with the steps of
  providing a compound (A) of the formula R3In2Cl3 according to one of claims 1 to 10;
  optionally isolating compound (A); wherein
the indium chloride component can, in particular, comprise: R2InCl, R3In2Cl3, RInCl$_2$ and mixtures thereof, or in particular Me2InCl, Et2InCl, MeInCl$_2$, EtInCl$_2$, Me3In2Cl3 or Et3In2Cl3 (where Et=ethyl and Me=methyl).

The present patent application further relates to a process for preparing trialkyl indium of the formula R3In, where R is an alkyl radical having 1 to 4 carbon atoms, the alkyl radical can be branched or unbranched and can, in particular, be ethyl or methyl, comprising the steps of
  providing a compound (A) according to one of claims 1 to 10;
  optionally isolating compound (A);
  reacting compound (A) with an alkylating agent to form compound (B), and
  optionally isolating and further purifying it.

In particular, the high yield and purity, and also cost-effective and comparatively environmentally benign process selection, in the process according to the invention makes the process ideally suited to the industrial preparation of compound (A) and, respectively, indium-containing precursors. In particular, no pyrophoric intermediates form in accordance with the invention, which is particularly advantageous in the light of cost-effective and low-complexity preparation. The process according to the invention is characterized, in particular, by an especially high indium exploitation. The overall conversion of indium in the process according to the invention, relative to the indium input, is preferably ≥70%, more preferably 75%, particularly preferably ≥80%, and even more preferably >95%. The oxygen content in the optionally obtainable compound (B) or (C), including indium alkoxides and oxides is preferably <100 ppm (m/m), in particular even <1 ppm (m/m).

The indium-containing precursors optionally preparable by the process according to the invention, in particular trimethyl indium and dimethylaminopropyl dimethyl indium, because of their excellent purity, in particular their very low oxygen content, are particularly suitable for MOCVD processes, for example for the preparation of semiconductors or semiconductor components. The semiconductors or semiconductor components ultimately produced have various possible industrial uses. Therefore, the invention also includes the use of compounds (B) and/or (C) optionally preparable in accordance with the invention as precursors for metal-organic chemical vapor phase deposition (MOCVD) or metal-organic vapor phase epitaxy (MOVPE).

WORKING EXAMPLES

Me3In2Cl3 (as compound A) was prepared according to the invention. MesIn as compound (B) was further produced from compound (A). In addition, dimethylaminopropyldimethylindium was prepared as compound (C).
  1. Preparation of Me3In$_2$Cl3
  1.1. Preparation of Methyl Indium Sesquichloride with Removal of Secondary Products During the Experiment 150.0 g (1.31 mol) of indium were provided in a 1l pressure reactor and the reactor was evacuated and vented to normal pressure with chloromethane. Next, 300.0 g Me3In2Cl3 (from a prior batch) were added to the reactor in liquid state via a drip funnel heated to 150° C. Then, chloromethane at 0.1 bar (overpressure, corresponding to 1.1 bar absolute) was added and the reaction mixture heated to 190° C. while stirring. In the process the indium and the Me3In2Cl3 melted. Starting at approximately 170° C. a strong gas uptake could be observed. Thereafter, the pressure was set to a nominal overpressure of 2 bar and supplemented with max. 0.5 l/min MeCl, as needed. After approximately four hours the gas uptake of the reaction decreased sharply. Thereafter, the MeCl supplementation to the reactor was suspended and the overpressure in the reactor was released via the exhaust line. Next, it was pressurized with MeCl to 3 bar overpressure and the reaction was continued. After 2.5 hours the gas uptake again sank to zero; a transparent yellow melt lay in the reactor, in which no more metallic indium could be seen. The gas supply was therefore stopped and the reactor cooled to room temperature overnight. The next day the reactor was reheated to 180° C. and pressurized to 2 bar overpressure with MeCl, although no further gas uptake occurred. To end the reaction, therefore, the gas inlet was closed, the stirrer turned off and the reaction mixture cooled to room temperature, whereby the reaction product congealed at approximately 100° C. The remaining overpressure of the reactor was released and the reactor evacuated to remove residual chloromethane and volatile secondary products. Next, the reactor was brought to normal pressure with argon, the reaction product was melted by heating to 150° C. and released from the reactor in liquid state. 545.7 g of product was obtained as a grayish-white solid. Purity according to NMR: 97.6%.

$^1$H-NMR (600 MHz, CD$_3$CN) δ=0.09 ppm (CH$_3$)$_2$InCl, 0.19 ppm (CH$_3$)InCl$_2$, in a ratio of 1.08:1; this corresponds to a composition of approximately 33% Me2InCl and 67% MeInCl$_2$. Elemental Analysis: in 58.8; C, 8.29; H, 2.13; Cl, 30.0. (calculated: In, 59.3; C, 8.4; H, 2.1; Cl, 30.2)
  1.2. Preparation of Methyl Indium Sesquichloride 300.0 g (2.61 mol) of indium were provided in a 1l pressure reactor, which was evacuated and ventilated to normal pressure with argon. Then, 150.0 g Me3In2Cl3 (from a previous batch) was added to the reactor as a solid in the argon counterflow. The reactor was again evacuated and 2.0 bar chloromethane (overpressure, corresponding to 3.0 bar absolute) was added and the reaction mixture heated to 200° C. while stirring. In doing so, the indium and the Me3In2Cl3 melted. The reaction started immediately, evidenced by a strong gas uptake and an orange coloration of the Me3In2Cl3. During the reaction, the MeCl was fed into the reactor according to consumption and to the set target overpressure at a maximum of 0.5 l/min. After approximately one hour the pressure was set to a target overpressure of 3 bar, and, after a further hour, the target overpressure was raised to 3.5 bar. After approximately three hours the reaction was suspended by cooling the reactor to room temperature overnight; small amounts of metallic indium were still visible in the reaction melt.

On the following day the MeCl target overpressure was set to 2.0 bar and the reaction restarted by heating to 200° C. and again introducing MeCl. After approximately two hours, the target overpressure was raised to 3.0 bar. After a further two hours, metallic indium could no longer be seen in the greenish-yellow reaction melt, although the reaction was continued for approximately 1.5 hours more until no more MeCl was taken up, The gas supply was closed, the overpressure in the reactor was released, and the resulting light brown melt was cooled in an MeCl atmosphere to room temperature, whereupon the reaction product congealed at approximately 100° C. Thereafter, the reactor was evacuated and subsequently gassed with argon in order to remove the remaining chloromethane and volatile secondary products. The solidified melt was remelted by heating to approximately 150° C. and released from the reactor in liquid state. 594.8 g of product were produced as a white solid. This corresponds to a yield of 91.5% relative to the total indium used (metallic indium+ $Me_3In_2Cl_3$). Purity per NMR was 99.1% $^1$H-NMR (600 MHz, $CD_3CN$) δ=0.08 ppm (CH3)2InCl, 0.17 ppm (CH3)InCl2, in a ratio of 1.5:1; this corresponds to a composition of approximately 40.5% Me2InCl and 59.5% MeInCb. Elemental Analysis: In, 59.7; Cl, 27.5; H, 2.3; C, 8.82 (calculated in 59.8; Cl, 29.0; H, 2.3; C, 8.7).

1.3. Preparation of Methyl Indium Sesquichloride 300.1 g (2.62 mol) of indium were charged in a 1l pressure reactor and the reactor was evacuated and vented to normal pressure with chloromethane. Then, 299.4 g Me3In2Cl3 (from a previous batch) were added into the reactor as a solid in the argon counterflow. Then, 2 bar chloromethane (overpressure, corresponding to 3 bar absolute) was added and the reaction mixture heated to 200° C. while stirring. In doing so, the Me3In2Cl3 and indium melted. The reaction started immediately, evidenced by an orange coloration of the liquid Me3In2Cl3 and the initiation of gas uptake. The pressure was thereafter set to a nominal overpressure of 3 bar and fed with a maximum of 0.5 l/min MeCl.

The reaction mixture was held at a reaction temperature of 190-200° C. until no more metallic indium was visible in the reactor.

The gas supply was then closed, the overpressure of the reactor was released and the resulting melt was cooled in an MeCl atmosphere to room temperature, whereupon the reaction product congealed at approximately 100° C. Thereafter, the reactor was evacuated and subsequently gassed with argon in order to remove the remaining chloromethane and volatile secondary products. The solidified reaction product was remelted by heating to 160° C. and released from the reactor in liquid state. 713.14 g of product were produced as a white solid. This corresponds to a yield of 90.2% relative to the total indium used (metallic indium+ $Me_3In_2Cl_3$), $^1$H-NMR (600 MHz, $CD_3CN$) δ=0.08 ppm $(CH_3)_2InCl$, 0.19 ppm (CH3)InC2, in a ratio of 1.3:1; this corresponds to a composition of approximately 37% $Me_2InCl$ and 63% $MeInCl_2$. Elemental Analysis: In, 60.1; Cl, 29.2; C, 8.6; H, 2.2. (calculated In, 59.6; Cl, 29.6; C, 8.7; H, 2.2). In addition, 66.71 g of a white solid could be scraped from the reactor cover (corresponding to 8.9% of the indium used), which was identified as dimethyl indium chloride (93% purity according to NMR). $^1$H-NMR (600 MHz, $CD_3CN$) δ=0.00 ppm $(CH_3)_2InCl$, Elemental Analysis: In, 64.0; Cl, 20.4; C, 12.9; H, 3.2. (calculated In, 63.3; Cl, 20.8; C, 12.8, H, 3.2).

1.4 Preparation of Methyl Indium Sesquichloride 150.0 g (1.31 mol) of indium were provided in a 1l pressure reactor and the reactor was evacuated and vented to normal pressure with chloromethane. Next, 300.0 g (0.79 mol) Me3In2Cl3 (from a previous batch) were added into the reactor in liquid state via a drip funnel heated to 150° C. Then, 0.3 bar chloromethane (overpressure, corresponding to 1.3 bar absolute) was added and the reaction mixture heated to 200° C. while stirring. In doing so, the indium melted. The reaction started immediately, evidenced by a strong gas uptake. The pressure was subsequently set to a target overpressure of 3 bar and a maximum of 0.5 l/min MeCl was fed in, although the gas uptake of the reaction was at first so strong that the target pressure could not be reached. After approximately three hours the reaction no longer took up any gas and no more metallic indium was visible in the reactor.

The gas supply was closed, the overpressure of the reactor was released, and the resulting light brown melt was cooled in an MeCl atmosphere to room temperature, whereupon the reaction product congealed at approximately 100° C. Thereafter, the reactor was evacuated three times and gassed each time with argon to remove the remaining chloromethane and volatile secondary products. The congealed melt was remelted by heating to approximately 150° C. and released from the reactor in liquid state.

540.49 g of product were produced as a white, slightly brownish solid. This corresponds to a yield of 98.8% relative to the total indium used (metallic indium+$Me_3In_2Cl_3$.

$^1$H-NMR (600 MHz, $CD_3CN$) δ=0.08 ppm $(CH_3)_2InCl$, 0.18 ppm $(CH_3)InCl_2$, in a ratio of 1.4:1; this corresponds to a composition of approximately 38% $Me_2InCl$ and 62% $MeInCl_2$. Elemental Analysis: In, 59.7; Cl, 29.8. (calculated In, 59.7; Cl, 29.3).

1.5 Preparation of Methyl Indium Sesquichloride (Semi-Continuous Experiment)

150.2 g (1.31 mol) of indium were charged in a 1l pressure reactor, which was evacuated, 353.0 g Me3Iri2Cl3 were released into the reactor in liquid state via a drip funnel. Next, the chloromethane supply was opened (nominal overpressure 3 bar) and the reaction mixture was heated to 200° C. while stirring. The reaction mixture was held at a reaction temperature of 190-200° C. for two and a half hours, until no more metallic indium was visible in the reactor and the reaction took up no more gas. The reaction mixture was stirred at reaction temperature for an additional two hours without gas supply, whereupon pressure in the reactor was relieved and 380 g Me3In2Cl3 in liquid state were released from the reactor. The rest of the Me3In2Cl3 (approximately 200 g) remained in the reactor. The reactor was cooled down to room temperature overnight. This procedure was repeated three times in succession. For this purpose, 150.0 g of indium were added each time to the Me3In2Cl3 remaining in the reactor, the reaction was restarted by heating to reaction temperature and restarting the gas supply and, according to the reaction time, approximately 250 g Me3In2Cl3 (corresponding to 1.3 mol indium) each time were released from the reactor twice. During the last procedure the experiment was ended by releasing all of the Me3In2Cl3 from the reactor. A total of 1280 g of Me3In2Cl3 were isolated. $^1$H-NMR (600 MHz, CD$_3$CN) δ=0.08 ppm (CH3)2InCl, 0.17 ppm (CH3)InCl2; average composition according to $^1$H-NMR: 40.2% Me$_2$InCl and 59.8% MeInCl$_2$. Elemental Analysis: In, 60.1; Cl28.8, corresponding to 6.67 mol Indium. This corresponds to a yield of 94.3% relative to the total indium used (7.07 mol).

2. Further Processing of Me$_3$In$_2$Cl$_3$ to give Me$_3$In 2.1. Reaction of Me$_3$In$_2$Cl$_3$ with MeLi to give LiInMe$_4$ 1430 mg of Me3In2Cl3 (3.75 mmol), were added to 12 ml of a MeLi solution (1.565 mol/L in diethyl ether) at 0° C. After approximately 1 h of stirring at room temperature, the suspension was filtered without celite and the filtrate freed from the solvent. 1128 mg of a colorless solid were isolated (corresponding to 6.2 mmol LiInMe$_4$, yield: 83%).

2.2. Reaction of LiInMe$_4$ with Me$_3$In$_2$Cl$_3$ to give Me$_3$In 947 mg of LiInMe$_4$ (5.2 mmol, from Example 2.1) and 660 mg of Me3In2Cl3 (1.73 mmol) were provided in a 125 ml Parr bomb and mixed with 10 ml of pentane. Thereafter, the Parr bomb was immersed in an oil bath preheated to 70° C. and stirred at that temperature for two hours. At 70° C. a clear liquid having gray solids (LiCl and impurities) could be observed which congealed to a crystal pulp upon cooling to room temperature. The liquid components of the Parr bomb were condensed in a cold trap (RT→–78° C.) and, thereafter, the pentane solvent was removed at –8° C. (sodium chloride and ice mixture) in a fine vacuum. It was possible to isolate 980 mg of a colorless solid, which was contaminated only with traces of lithium chloride. This corresponds to 6.1 mmol/yield: 70% trimethyl indium.

2.3. Reaction of LiInMe$_4$ with Me$_2$InCl to Form Me$_3$In 1079 mg of LiInMe$_4$ (5.9 mmol) and 1067 mg of Me2InCl (5.9 mmol) were provided in a 125 ml Parr bomb and mixed with 20 ml of pentane. Thereafter, the Parr bomb was immersed in an oil bath preheated to 70° C. and stirred at that temperature overnight. At 70° C. a slightly turbid suspension could be observed which congealed to a crystal paste upon cooling to room temperature. The volatile components of the Parr bomb were condensed in a cold trap (RT→–78° C.) and thereafter the pentane solvent was removed at –8° C. (sodium chloride and ice mixture) in a fine vacuum. It was possible to isolate 1591 mg of a colorless solid (10.0 mmol, yield: 81% trimethyl indium).

2.4. Synthesis of Trimethyl Indium from Me$_3$In$_2$Cl$_3$ 3.36 g (8.8 mmol) of Me3In2Cl3 and 3.19 g (54.9 mmol) of KF in 20 ml of squalene were provided in a 100 ml three-necked flask under protective gas. 2.05 g (28.4 mmol) of MesAl, dissolved in 6 ml of squalene, were added dropwise via a drip funnel while stirring. Following complete addition, the reaction mixture was heated to 80° C. for 3 hours, whereupon fine, colorless crystals were already precipitating on the colder surfaces of the flask. Thereafter, a vacuum was carefully drawn over the apparatus and the trimethyl indium was sublimated into a receiving flask cooled with liquid nitrogen. It was possible to isolate 2.60 g (16.3 mmol, 92.6% yield) of trimethyl indium as a colorless, crystalline solid. The product obtained still contained small amounts of MesAl as an impurity. $^1$H-NMR (CeD$_6$): –0.23 ppm (CH$_3$)3In.

2.4. Synthesis of Trimethyl Indium from Me$_3$In$_2$Cl$_3$ In the Grignard Reaction 10.0 g (26.2 mmol) of Me3Iri2Cl3 in 50 ml of dry THF were provided under protective gas in a 250 ml three-necked flask with reflux condenser. 27.1 ml (81.2 mmol, 3.1 eq.) of a 3 molar MeMgI solution in diethyl ether were slowly added dropwise via a drip funnel in such a way that a constant reflux was created. Following the end of the addition, the reaction mixture was heated for yet another hour under reflux to complete the reaction. Thereafter, the reaction mixture was cooled to room temperature, and the drip funnel and reflux condenser were removed from the flask and replaced by a receiving flask cooled with liquid nitrogen. The resulting trimethylindium diethyl ether adduct was distilled into the receiving flask in a vacuum under slow warming of the reaction vessel to 180° C. To isolate trimethylindium, some dry benzene was then added to the adduct and the solvent was separated by fractional distillation in a Vigreux column.

3. Further Processing of Me$_3$In$_2$Cl$_3$ to Dimethylaminopropyl Dimethyl Indium (DADI)

3.1. Separation of Me$_2$InCl from Me$_3$In$_2$Cl$_3$ by Sublimation 1050 mg (2.76 mmol) of Me3In2Cl were immersed overnight in a Schlenk flask in an oil bath heated to 170-180° C. A colorless solid resublimated on the colder regions of the Schlenk flask. After cooling to room temperature, a cooled melt could be observed on the bottom. Mass of the sublimated solid (Me2InCl, identified via $^1$H-NMR): 160 mg (0.89 mmol, yield: 32%). Mass of the cooled melt: 860 mg.

3.2 Separation of Me$_2$InCl from Me$_3$In$_2$Cl$_3$ by Sublimation in the Presence of KCl 1.60 g (4.20 mmol) of Me3In2Cl3, together with 0.44 g (5.91 mmol) of KCl, were melted together in a Schlenk flask fitted with a sublimation tube at 140° C. until a clear homogeneous melt was obtained. After cooling to room temperature, the entire system was evacuated to 10$^{-3}$ mbar and the congealed melt was slowly heated to 190° C. Thereupon, the solid began to melt and, at the same time, the resublimation of a colorless solid could be observed in the sublimation tube. After approximately two hours the melt had transformed into a colorless solid and the sublimation came to an end. From the sublimation pipe, 1.12 g (6.22 mmol), yield: 99%) Me2InCl could be obtained as a colorless solid, identified via 1H-NMR.

3.3. Reaction of Me$_2$InCl with Dimethylaminopropyl Magnesium Chloride

In a 500 ml three-neck flask, 150 ml of dried THF and 5.26 g (216 mmol, 1.95 equiv.) of magnesium shavings were received and heated to reflux.

Following addition of a spatula tip of iodine to activate the magnesium, 15.55 g (126 mmol, 1.14 equiv.) of 3-Dimethylaminopropylchloride were slowly added dropwise, and the reaction mixture was then heated under reflux for an additional 2.5 h. Following cooling of the reaction mixture to room temperature, 20.00 g (111 mmol) Me2InCl dissolved in 150 ml dried THF was added dropwise within 30 minutes and the resulting reaction solution was stirred for 20 hours at room temperature.

Thereafter, the THF was removed in a vacuum, the residue was suspended in 100 ml of dried hexane, stirred at room temperature for 2 h, the resulting white solid was separated using a reverse frit and washed twice, each time with 50 ml of dried hexane. The clear filtrate was concentrated to dryness in a vacuum and distilled for purification at 80° C. and 5 mbar. DADI was obtained as a clear liquid (19.7 g, 85.3 mmol, yield: 77%).

3.4 Reaction of Me₂InCl with 3-Dimethylaminopropyl-lithium

In a 500 ml three-neck flask, 75 ml of dried THF and 1.16 g (170 mmol, 3 equiv.) lithium shavings were received and heated to reflux.

After reaching reflux, 10.12 g (83.2 mmol, 1.5 equiv.) 3-Dimethylaminopropylchloride were slowly added dropwise, and the reaction mixture was then heated under reflux for an additional 2.5 h. Following cooling of the reaction mixture to room temperature, 10.00 g (55.4 mmol) Me2InCl dissolved in 75 ml dried THF were added dropwise within 30 minutes and the resulting reaction solution was stirred for 20 hours at room temperature.

Thereafter, the THF was removed in a vacuum, the residue was suspended in 100 ml of dried pentane, stirred at room temperature for 2 h, and the resulting white solid was separated using a reverse frit and washed twice, each time with 50 ml dried pentane. The clear filtrate was concentrated to dryness in vacuum and distilled for purification at 80° C. DADI was obtained as a clear liquid.

The invention claimed is:

1. Process for preparing a compound (A) having the general formula:

R₃In₂Cl₃ comprising the reaction steps of
a1) reacting indium with an alkyl donor to form compound (A), wherein the alkyl donor is alkyl chloride (RCl) and wherein R is a branched or unbranched alkyl radical having 1 to 4 carbon atoms,
a2) and optionally isolating compound (A) from the reaction mixture;
wherein a compound having the formula R₃In₂Cl₃ is used as reaction medium and the ratio of indium to the reaction medium is 0.5:10 to 1.4:0.5 (relative to weight).

2. Process according to claim 1, wherein R is methyl or ethyl.

3. Process according to claim 1, wherein the molar ratio of indium to the compound having the formula R₃In₂Cl₃ is 1:1 to 8:1.

4. The process of claim 3, wherein the molar ratio of indium to the compound having the formula R₃In₂Cl₃ is 1:1 to smaller than 4:1.

5. Process according to claim 3, wherein the molar ratio of indium to the compound having the formula R₃In₂Cl₃ is 1:1 to 3.8:1.

6. The process of claim 5, wherein the molar ratio of indium to the compound having the formula R₃In₂Cl₃ is 1:1 to 3.5:1.

7. Process according to claim 1, wherein the compound having the formula R₃In₂Cl₃ is a combination of dialkyl indium chloride (R₂InCl) and alkyl indium dichloride (RInCl₂).

8. Process according to claim 7, wherein the compound having the formula R₃In₂Cl₃ is a combination of dialkyl indium chloride (R₂InCl) and alkyl indium dichloride (RInCl₂) having a molar ratio of 30:70 to 50:50.

9. The process of claim 8, wherein the compound having the formula R₃In₂Cl₃ is a combination of dialkyl indium chloride (R₂InCl) and alkyl indium dichloride (RInCl₂) having a molar ratio of 32:68 to 42:58.

10. Process according to claim 1, wherein gaseous alkyl chloride is used as the alkyl donor.

11. Process according to claim 1, wherein 1.5 to 5 equivalents of alkyl donor are used per equivalent of indium.

12. The process of claim 11, wherein 1.65 to 2.9 equivalents of alkyl donor are used per equivalent of indium.

13. Process according to claim 1, wherein the indium in reaction step a1) is provided in a reaction vessel and the alkyl donor is subsequently added.

14. Process according to claim 13, wherein the alkyl donor is added at temperatures above 20° C. and at an overpressure of 0.1 bar to 6 bar.

15. Process according to claim 1, wherein the reaction temperature is 160° C. to 220° C.

16. Process according to claim 1, wherein the process comprises the isolation of compound (A) as step a2), and wherein the said isolation comprises the separation of volatile secondary constituents from the reaction mixture present in the reaction vessel and the subsequent removal of compound (A) from the reaction vessel.

17. Process for preparing a compound (B) having the general formula

R₃In, wherein R is a branched or unbranched alkyl radical having 1 to 4 carbon atoms, comprising the reaction steps of
providing compound (A) according to claim 1;
reacting compound (A) with alkylating agent to form compound (B).

18. Process according to claim 17, wherein the alkylating agent is selected from R—MgX, R—Li and R₃Al, wherein R is a branched or unbranched alkyl radical having 1 to 4 carbon atoms.

19. Process for preparing a compound (B) having the general formula

R₃In, comprising the reaction steps of
b0) providing compound (A) according to claim 1;
b1) reacting compound (A) with an alkyllithium to form lithium tetraalkylindate (LiInR₄), and isolating LiInR₄ from the reaction mixture, and
b2) reacting LiInR₄ with an indium chloride component to obtain compound (B), wherein R is a branched or unbranched alkyl radical having 1 to 4 carbon atoms.

20. Process according to claim 19, wherein the indium chloride component has the general formula:

R_aIn_bCl_c wherein a is a number selected from 0, 1, 2, and 3, and b is a number selected from 1 and 2, and c is a number selected from 1, 2, and 3, and wherein a+b+c=4 or a multiple of 4, and wherein R is an alkyl radical having 1 to 4 carbon atoms, and wherein R is branched or unbranched.

21. Process according to claim 19, wherein the indium chloride component is selected from R2InCl, R₃In₂Cl₃, RInCl₂, InCl₃, and mixtures thereof.

22. Process for preparing a compound (C) having the general formula:

R₂InR' comprising the following reaction steps:
c0) providing compound (A) according to claim 1;
c1) separating dialkyl indium chloride from compound (A), wherein the dialkyl indium chloride satisfies the general formula:

R₂InCl,
wherein R is defined as above; and c2) reacting $R_2InCl$ with an alkylating agent to form compound (C), wherein R' is a nucleophilic radical selected from the group consisting of branched or unbranched and substituted or unsubstituted alkyl, branched or unbranched and substituted or unsubstituted aryl, which can be substituted with branched or unbranched alkyl or alkoxy groups, or with amine radicals.

23. Process according to claim 22, wherein the alkylating agent is selected from R'MgX, and R'$_3$Al.

24. Process according to claim 22, wherein R is methyl, and wherein R' is a $Me_2N\text{---}(CH_2)_3$ group or an ethyl group.

25. Process for preparing an indium chloride component having the general formula:

$R_aIn_bCl_c$, where a is a number selected from 0, 1, 2, and 3, and b is a number selected from 1 and 2, and c is a number selected from 1, 2, and 3, and where a+b+c=4 or a multiple of 4, where R is an alkyl radical having 1 to 4 carbon atoms, the alkyl radical can be branched or unbranched, with the steps of providing a compound (A) of the formula $R_3In_2Cl_3$ according to claim 1;

optionally isolating compound (A); wherein the indium chloride component comprises: $R_2InCl$, $R_3In_2Cl_3$, $RInCl_2$ and mixtures thereof.

26. Process for preparing trialkylindium having the formula $R_3In$, wherein R is an alkyl radical having 1 to 4 carbon atoms, the alkyl radical can be branched or unbranched, comprising the steps of providing a compound (A) according to claim 1;
optionally isolating compound (A);
reacting compound (A) with an alkylating agent to form compound (B), and
optionally isolating and further purifying it.

27. The process of claim 1, wherein the ratio of indium to the reaction medium is 0.5:3 to 1.4:0.5 (relative to weight).

28. The process of claim 1, wherein the ratio of indium to the reaction medium is 1:2 to 2:1 (relative to weight).

29. The process of claim 1, wherein the ratio of indium to the reaction medium is 1:1.5 to 1.5:1 (relative to weight).

* * * * *